United States Patent
Wang

(10) Patent No.: US 10,435,477 B2
(45) Date of Patent: Oct. 8, 2019

(54) PROPROTEIN CONVERTASE SUBTILISIN KEXIN TYPE 9 BINDING PROTEINS AND USES THEREOF

(71) Applicant: MAB-SCIENCE (HONG KONG) LIMITED, Hong Kong (CN)

(72) Inventor: Shaoxiong Wang, Hong Kong (CN)

( * ) Notice: Subject to any disclaimer, the term of this patent is extended or adjusted under 35 U.S.C. 154(b) by 0 days.

(21) Appl. No.: 16/091,953

(22) PCT Filed: Apr. 7, 2017

(86) PCT No.: PCT/CN2017/079655
§ 371 (c)(1),
(2) Date: Oct. 5, 2018

(87) PCT Pub. No.: WO2017/174017
PCT Pub. Date: Oct. 12, 2017

(65) Prior Publication Data
US 2019/0119404 A1    Apr. 25, 2019

(30) Foreign Application Priority Data

Apr. 7, 2016 (CN) .......................... 2016 1 0213460

(51) Int. Cl.
| | | |
|---|---|---|
| *C07K 16/40* | (2006.01) | |
| *G01N 33/577* | (2006.01) | |
| *A61K 47/68* | (2017.01) | |
| *A61P 7/02* | (2006.01) | |
| *A61P 9/10* | (2006.01) | |
| *A61P 3/06* | (2006.01) | |
| *C12N 15/62* | (2006.01) | |
| *G01N 33/52* | (2006.01) | |
| *A61K 39/00* | (2006.01) | |

(52) U.S. Cl.
CPC .......... *C07K 16/40* (2013.01); *A61K 47/6891* (2017.08); *A61P 3/06* (2018.01); *A61P 7/02* (2018.01); *A61P 9/10* (2018.01); *C12N 15/62* (2013.01); *G01N 33/52* (2013.01); *G01N 33/577* (2013.01); *A61K 2039/505* (2013.01); *C07K 2317/21* (2013.01); *C07K 2317/33* (2013.01); *C07K 2317/92* (2013.01); *C07K 2317/94* (2013.01); *C12Y 304/21* (2013.01)

(58) Field of Classification Search
None
See application file for complete search history.

(56) References Cited

U.S. PATENT DOCUMENTS

2009/0142352 A1* 6/2009 Jackson ................. A61K 31/22
424/139.1

FOREIGN PATENT DOCUMENTS

| CN | 102333542 A | 1/2012 |
|---|---|---|
| CN | 104364266 A | 2/2015 |
| CN | 104861071 A | 8/2015 |
| WO | 2013/169886 A1 | 11/2013 |

OTHER PUBLICATIONS

WIPO; International Search Report issued in International Publication No. WO2017/174017, dated Oct. 12, 2017.
WIPO; Written Opinion issued in International Publication No. WO2017/174017, dated Oct. 12, 2017.

\* cited by examiner

*Primary Examiner* — Sharon X Wen
(74) *Attorney, Agent, or Firm* — Snell & Wilmer L.L.P.

(57) ABSTRACT

Provided herein is a proprotein convertase subtilisin kexin type 9 (PCSK9)-specific binding protein that comprises unique complementary determining regions, that is capable of specifically binding to PCSK9, effectively inhibiting the function of PCSK9, lowering plasma LDL cholesterol level and that is useful in treating diseases associated with or impacted by the function of PCSK9.

15 Claims, 2 Drawing Sheets
Specification includes a Sequence Listing.

Human PCSK9

Monkey PCSK9

Mouse PCSK9

PROPROTEIN CONVERTASE SUBTILISIN KEXIN TYPE 9 BINDING PROTEINS AND USES THEREOF

CROSS-REFERENCE TO RELATED APPLICATIONS

This application is the national stage entry of International Application No. PCT/CN17/079655, entitled PROPROTEIN CONVERTASE SUBTILISIN KEXIN TYPE 9 BINDING PROTEIN AND APPLICATION THEREOF, and filed Apr. 7, 2017, which claims the benefit of Chinese Patent Application No. 201610213460.1, entitled PROPROTEIN CONVERTASE SUBTILISIN KEXIN TYPE 9 BINDING PROTEIN AND APPLICATION THEREOF, and filed Apr. 7, 2016, the disclosures of which, including any appendices, are incorporated herein by reference to the extent such disclosures do not conflict with the present disclosure.

SEQUENCE LISTING

The instant application contains a Sequence Listing which has been submitted electronically in computer readable form (in text format). The name of the text file containing the Sequence Listing is 7679800100_SL.txt and is hereby incorporated by reference in its entirety.

FIELD OF THE INVENTION

This disclosure relates to proprotein convertase subtilisin kexin type 9 (PCSK9) binding proteins and uses thereof in the field of immunology.

BACKGROUND OF THE INVENTION

Cardiovascular diseases are the first leading cause of mortality in human beings. Low-density lipoprotein cholesterol (LDL-C) has been shown as one of the major risk factors of cardiovascular diseases, while its effect is relatively independent and controllable. In the past twenty years, statin-based lipid-lowering drugs have been successfully used to reduce incidence of cardiovascular diseases.

Nevertheless, statins are not always effective, and there are different needs of hypolipidemic therapy. Some patients, especially those of familial hypercholesterolaemia (FH) do not respond to statins. In these patients, it's difficult to control LDL-C at a low level even with a high dosage of statins. Besides, statins are associated of side effects including myalgia and rhabdomyolysis, which makes them intolerable or only tolerable at a very low dosage for some of the patients in need of blood lipid control. Then, proprotein convertase subtilisin kexin type 9 (PCSK9) inhibitors were found as a novel class and a new option of medication for control of blood LDL-C concentration.

PCSK9 is a serine protease, which plays a role in modulation of low-density lipoprotein receptor (LDLR). It has been shown in vitro that the level of cell surface LDLR is decreased in HepG2 cells when treated with PCSK9 protein. In vivo experiments in mice suggested that an increased level of PCSK9 protein reduced LDLR expression in liver. At the same time, compared to normal mice, PCSK9-knockout mice exhibited an increased level of LDLR. It has been shown that PCSK9 directly binds to LDLR to be internalized together via immunofluorescence in the process of endocytosis. Up till now, there is no direct evidence of extracellular LDLR degradation by PCSK9, and the mechanism for PSCK9 in lowering the LDLR protein level remains elusive.

Studies have shown that PCSK9 plays a role in modulation of LDL production. Expression or up-regulation of PCSK9 has been associated with increased plasma LDL cholesterol, while expression suppression or deficiency of PCSK9 with decreased plasma LDL cholesterol.

Therefore, it is of great significance to develop therapeutic PCSK9 antagonists that inhibit or antagonize PCSK9 activities and importantly, monoclonal antibodies that specifically bind to PCSK9. Largely, PCSK9 inhibitors currently under investigation include small interfering RNA (siRNA), antisense oligonucleotides (ASOs), monoclonal antibodies and fusion proteins with binding specificity generated from new platforms, such as fusion proteins generated by the Adnectin platform. Currently, the major PCSK9 inhibitors include siRNA drugs, such as RG7652 (Alnylam Pharmaceuticals/The Medicines Company); Adnectin fusion proteins, such as BMS-962476 (BMS); ASO drugs, such as ALN-PCS02 (Idera Pharmaceuticals); antibody drugs, such as Bococizumab (Pfizer/Rinat) and LGT-209(Novartis); etc.

However, as found in some animal experiments and clinical investigations, some monoclonal antibodies as PCSK9 inhibitors still have problems with specificity, affinity or side effects. Therefore, there is a need for improved novel anti-PCSK9 antibodies with better efficacy.

SUMMARY OF THE INVENTION

An objective of the present invention is to provide a proprotein convertase subtilisin kexin type 9 (PCSK9)-binding protein and uses thereof.

In the first aspect of the disclosure, provided herein is a PCSK9-specific binding protein comprising a light-chain variable region and a heavy-chain variable region, wherein,
  the CDR1 of the heavy-chain variable region has the amino acid sequence as set forth in SEQ ID NO: 7;
  the CDR2 of the heavy-chain variable region has the amino acid sequence as set forth in SEQ ID NO: 8;
  the CDR3 of the heavy-chain variable region has the amino acid sequence as set forth in SEQ ID NO: 9 or the amino acid sequence as set forth in SEQ ID NO: 13;
  the CDR1 of the light-chain variable region has the amino acid sequence as set forth in SEQ ID NO: 10;
  the CDR2 of the light-chain variable region has the amino acid sequence as set forth in SEQ ID NO: 11; and
  the CDR3 of the light-chain variable region has the amino acid sequence as set forth in SEQ ID NO: 12.

In a preferred embodiment, the PCSK9-specific binding protein is selected from the group consisting of those wherein:
  (a) the CDR1, CDR2 and CDR3 of the heavy-chain variable region have the amino acid sequences as set forth in SEQ ID NO: 7, SEQ ID NO: 8 and SEQ ID NO: 9, respectively; and the CDR1, CDR2 and CDR3 of the light-chain variable region have the amino acid sequences as set forth in SEQ ID NO: 10, SEQ ID NO: 11 and SEQ ID NO: 12, respectively; or
  (b) the CDR1, CDR2 and CDR3 of the heavy-chain variable region have the amino acid sequences as set forth in SEQ ID NO: 7, SEQ ID NO: 8, SEQ ID NO: 13, respectively; and the CDR1, CDR2 and CDR3 of the light-chain variable region have the amino acid sequences as set forth in SEQ ID NO: 10, SEQ ID NO: 11 and SEQ ID NO: 12, respectively.

In another preferred embodiment, the PCSK9-specific binding protein comprises: a heavy-chain variable region and a light-chain variable region having the amino acid sequences as set forth in SEQ ID NO: 2 and SEQ ID NO: 4, respectively; or a heavy-chain variable region and a light-chain variable region having the amino acid sequences as set forth in SEQ ID NO: 6 and SEQ ID NO: 8, respectively.

In another preferred embodiment, the binding protein is an Fab, an F(ab'), an F(ab')2, an Fv, a dAb, an Fd, a complementary determining region (CDR) fragment, a single-chain antibody (scFv), a divalent single-chain antibody, a single-chain phage antibody, a bispecific diabody, triabody, or tetrabody.

In another preferred embodiment, the binding protein is a monoclonal antibody.

In another preferred embodiment, the heavy-chain variable region and the light-chain variable region of the binding protein have the amino acid sequences as set forth in SEQ ID NO: 2 (with a leader peptide) and SEQ ID NO: 4 (with a leader peptide), respectively; or have the amino acid sequences as set forth in SEQ ID NO: 6 (with a leader peptide) and SEQ ID NO: 4, respectively; or the amino acid sequences as set forth in SEQ ID NO: 22 (without leader peptide) and SEQ ID NO: 24 (without leader peptide), respectively; or the amino acid sequences as set forth in SEQ ID NO: 26 and SEQ ID NO: 24, respectively. The heavy-chain constant region is one of the subclass selected from IgG1, IgG2a, IgG2b or IgG3, and the light-chain constant region is of type κ or type λ.

In another aspect, provided herein is a nucleic acid encoding the PCSK9-specific binding protein.

In another aspect, provided herein is an expression vector comprising the nucleic acid.

In another aspect, provided herein is a host cell comprising the expression vector or the nucleic acid integrated into the genome of the cell.

In another aspect, provided herein is use of the PCSK9-specific binding protein for manufacturing a medicament for diagnosing, treating and/or preventing a disease associated with abnormal expression or activity of PCSK9.

In a preferred embodiment, diseases associated with abnormal expression or activity of PCSK9 include but are not limited to: conditions associated with high serum cholesterol, particularly, for example, hypercholesterolemia, coronary heart disease, metabolic syndrome, acute coronary syndrome.

In another aspect, provided herein is a pharmaceutical composition comprising an effective amount of the PCSK9-specific binding protein and a pharmaceutically acceptable vehicle.

In another aspect, provided herein is a kit for treating and/or preventing a disease associated with abnormal expression or activity of PCSK9. In an embodiment, the kit comprises the PCSK9-specific binding protein or the pharmaceutical composition as described above.

In another aspect, provided herein is an immunoconjugate comprising the PCSK9-specific binding protein and a detectable label. Preferably, suitable detectable labels include fluorescent labels and chromogenic labels.

In another aspect, provided herein is a detection kit for detecting the level of PCSK9. In an embodiment, the detection kit comprises the PCSK9-specific binding protein or the immunoconjugate as described above.

Other aspects of the invention will be apparent to a person of ordinary skills in the art from this disclosure.

DETAILED DESCRIPTION OF THE INVENTION

Figure 1:
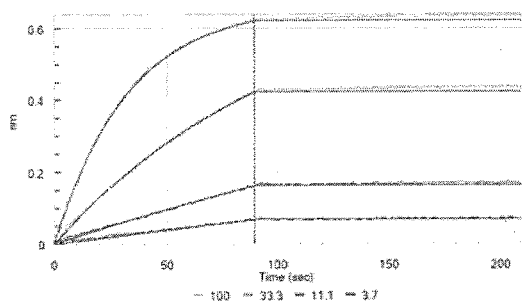
FIG. 1: kinetics analysis results of monoclonal antibodies B9287 and B9288 against human PCSK9 antigen, mouse PCSK9 antigen and *Macaca fascicularis* PCSK9 antigen, respectively.
Figure 1:
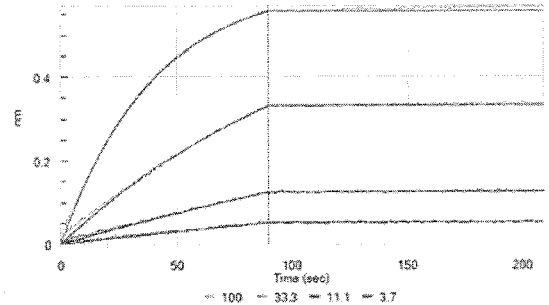
Figure 1:
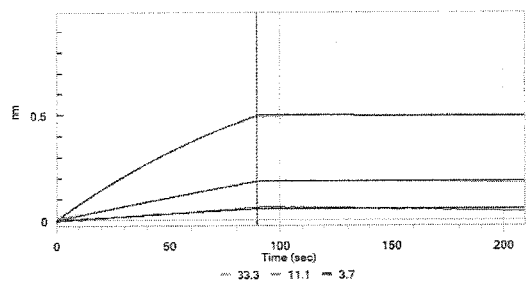
Figure 1:
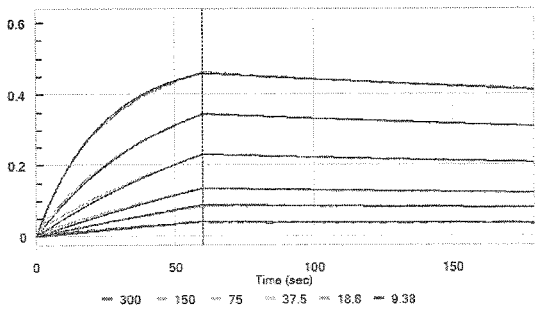

The inventors obtained through extensive and intensive investigation a binding protein specifically binding to proprotein convertase subtilisin kexin type 9 (PCSK9), which features unique complementary determining regions (CDRs). The binding protein is capable of specific binding to PCSK9 to effectively inhibit the function of PCSK9, and capable of decreasing plasma LDL cholesterol level. The binding protein is useful in treating diseases associated with or impacted by the function of PCSK9.

Binding Protein

In one aspect, provided herein is a PCSK9-specific binding protein. The binding proteins of the invention may be a whole immunoglobulin molecule or an antigen binding fragment thereof. Examples include, but are not limited to an Fab fragment, an Fd fragment, an Fv fragment, an F(ab')2 fragment, a complementary determining region (CDR) fragment, a single-chain antibody (scFv), a domain antibody, a divalent single-chain antibody, a single-chain phage antibody, a bispecific diabody, triabody and tetrabody.

CDR regions are protein sequences of immunological interests. In some embodiments of the present invention, the binding protein may comprise two, three, four, five or six CDR regions according to the present disclosure. Preferably, the binding protein comprises at least two CDRs according to the present disclosure.

As another aspect of the invention, included herein are functional variants of a binding protein of the invention, which are identified by their capability of competing with the parent binding protein for the specific binding to PCSK9. In other words, the functional variants are also capable of binding to PCSK9 or a fragment thereof. The functional variants include but are not limited to those having an essentially similar primary sequence but with one or more chemical and/or biochemical modification(s) occurred in vitro or in vivo that are not found in the parent binding protein. These modifications include, for example, acetylation, acylation, covalent attachment of nucleotides or nucleotide derivatives, covalent attachment of lipids or lipid derivatives, cross-linking, disulfide bond formation, glycosylation, hydroxylation, methylation, oxidation, PEGylation, proteolytic processing, phosphorylation, etc. In other words, as compared to the binding property of the parent, the modification(s) in the amino acid sequence and/or nucleotide sequence of the parent binding protein, do not significantly impact or change the binding property of the binding protein(s) encoded by the modified nucleotide sequence or the amino acid sequence. That is, the modified binding proteins retain the capability of recognizing and binding to the corresponding target sites.

A functional variant may comprise conservative modification(s) in sequence, such as substitution, addition and deletion of nucleotide(s) or amino acid(s). These can be introduced using standard techniques such as directed mutagenesis and PCR-mediated random mutagenesis, and may include natural and unnatural amino acids or nucleotides.

Conservative amino acid substitution may include replacement with a different amino acid residue with similar structure or chemistry. Families of amino acid residues with similar side groups have been well characterized, which include: amino acids with basic side groups (e.g., lysine, arginine, histidine); amino acids with acidic side groups (e.g., aspartic acid, glutamic acid); amino acids with uncharged polar side groups (e.g., aspartate, glutamine, serine, threonine, tyrosine, cysteine, tryptophan); amino acids with non-polar side groups (e.g., glycine, alanine, valine, leucine, isoleucine, valine, proline, phenylalanine, methionine); amino acids with branched side groups (e.g., threonine, valine, isoleucine); and amino acids with aromatic side groups (e.g., tyrosine, phenylalanine, tryptophan). It should be understood that amino acid families can be classified in different ways other than the above. Additionally or alternatively, a variant may comprise non-conservative amino acid substitution(s), such as replacement with a different amino acid having dissimilar structure or chemistry. Similar minor variation may further be included, like amino acid deletion or insertion or both. Computer implemented programs have been developed and widely used to scan for the amino acid residue(s) that can be substituted, inserted or deleted without loss of immunological activity.

Functional variants also include amino acid sequences truncated at the amino-end or the carboxyl-end or both. According to the present invention, a functional variant may have an identical or different (either higher or lower) binding affinity compare to the parent binding protein, as long as it retains the capability of binding to PCSK9 or a fragment thereof. For instance, a functional variant may have a decreased or preferably an increased binding affinity to PCSK9 or a fragment thereof, compared to the parent binding protein. Preferably, a variable region may comprise modification(s) in amino acid sequence in one or more of the region(s) including, but not limited to frame regions, hypervariable regions or CDR regions. Normally, the light-chain and the heavy-chain variable regions each comprise three hypervariable regions each comprising three CDRs and more conservative frame regions (FRs). The hypervariable region includes the amino acid residues of the CDRs and hypervariable loops. In the context of the present invention, a functional variant may have an amino acid sequence identity of at least about 50% to about 99% with the parent binding protein, preferably at least about 60% to about 99%, more preferably at least about 70% to about 99%, even more preferably at least about 80% to about 99%, most preferably at least about 90% to about 99%, particularly at least about 95% to about 99%, and particularly at least about 97% to about 99%. Computer implemented algorithms, such as Gap and Bestfit, can be used to calculate similar or identical residues via best alignment. Functional variants can be obtained by modifying the parent binding protein or a portion thereof using general molecular biological methods as known to a person of ordinary skills in the art, which include, but are not limited to error-prone PCR, oligonucleotide-directed mutagenesis, site-directed mutagenesis, and heavy chain and/or light-chain recombination.

As a preferred embodiment of the invention, the binding protein is a monoclonal antibody. For an antibody, its antigen-binding property is defined by the three unique regions called "complementary determining regions (CDRs)" in each of the heavy-chain and the light-chain variable regions. The CDRs are separated by four frame regions (FRs) in the variable region. The four FRs are relatively conservative in amino acid sequence and do not directly participate the binding reaction. The CDRs each form a ring structure and are drawn close to one another in configuration by the beta-sheets formed by the intermediate FRs. The CDRs of the heavy-chain together with the corresponding CDRs of the light-chain form the antigen binding site of the antibody. The CDRs in the anti-PCSK9 monoclonal antibody according to the invention are new, which are different from any of those in the existing anti-PCSK9 antibodies.

The monoclonal antibodies of the invention are fully human ones, which have decreased immunogenicity and increased safety.

In another aspect, provided herein is a nucleic acid molecule encoding at least one of the binding proteins, the functional variants thereof or the immunoconjugates according to the present invention. The nucleic acid molecule can be used as an intermediate for cloning, for example in the affinity maturation as previously described. In a preferred embodiment, the nucleic acid molecule is isolated and/or purified. The sequence of the DNA molecule can be obtained using conventional means, such as the hybridoma technique.

The obtained sequence can then be amplified using recombinant techniques. This is normally done by cloning the sequence into a vector to be transferred into a host cell and isolating the amplified sequences from the host cells after proliferation.

Alternatively, the sequence may be synthesized, especially in the case of a relatively short fragment. Normally, a long fragment may be assembled from synthesized shorter fragments.

The DNA sequence encoding the binding protein (or a fragment or a derivative thereof) according to the invention can be wholly synthesized. The DNA sequence may then be incorporated or introduced into suitable DNA molecules (or, e.g., vectors) and cells as appropriate. Alternatively, mutations may also be introduced into the sequence of the binding protein via chemical synthesis.

Also included herein is a vector comprising a suitable DNA sequence as described above and a suitable promoter or regulatory sequence. The vector may be used to transform a suitable host cell to express the protein. Preferably, the vector is, for example, a plasmid expression vector with a viral promoter, which comprises an insert for a fusion sequence of the heavy-chain variable region (VH) of the anti-PCSK9 monoclonal antibody and the constant region of IgG2 (derived from human IgG2) and an insert for a fusion sequence of the light-chain variable region (VL) and a human Ig Lambda sequence (derived from the constant region of human Ig lambda).

The host cell may be a prokaryotic cell (e.g., a bacterial cell), a lower eukaryotic cell (e.g., a yeast cell) or a higher eukaryotic cell (e.g., a mammalian cell). Representative examples include bacterial cells, such as *Escherichia coli, Streptomyces* and *Salmonella typhimurium*; fungal cells, such as yeasts; plant cells; insect cells, such as Drosophila S2 or Sf9 cells; animal cells, such as CHO, COST, NSO or Bowes melanoma cell, etc. Particularly suitable are eukaryotic host cells, more particularly, mammalian cells, such as CHO cells and 293 cells.

Optionally, the recombinant binding protein may be isolated and purified based on certain physical, chemical and/or other properties of the protein as desired. Useful methods are well known to a person of ordinary skills in the art, which may include, but are not limited to for example, conventional renaturation, protein precipitation (e.g., salting out), centrifugation, osmotic bacteriolysis, sonication, ultracentrifugation, molecular sieve chromatography (gel filtration), adsorptive chromatography, ion exchange chromatography, high performance liquid chromatography (HPLC), various liquid phase chromatographies, and combinations thereof.

Pharmaceutical Composition

The binding molecule according to the invention can be used for preparing a pharmaceutical composition useful in diagnosing, treating and/or preventing diseases associated with abnormal expression or activity of PCSK9.

The term "diseases associated with abnormal expression or activity of PCSK9" includes conditions associated with high serum cholesterol. Particularly, the "diseases associated with abnormal expression or activity of PCSK9" include, but are not limited to hypercholesterolemia, coronary heart disease, metabolic syndrome, acute coronary syndrome and correlated disorder and/or symptoms. The term "activity of PCSK9" and "PCSK9 activity" are used exchangeably as referring to whatever events or functions involving, exacerbated or enhanced by PCSK9. The anti-PCSK9 monoclonal antibody is also useful in detection and quantification of PCSK9 for diagnostic purposes.

Based on the new finding here, also provided is a pharmaceutical composition for diagnosing, treating and/or preventing diseases associated with abnormal expression or activity of PCSK9, which comprises an effective amount of a binding molecule according to the invention and a pharmaceutically acceptable vehicle.

As used herein, the term "pharmaceutically acceptable" means that the relevant molecule and the composition comprising the same do not cause an undesired effect such as allergy when being administered to an animal or human subject. As used herein, a "pharmaceutically acceptable vehicle" should be compatible with the binding molecule of the invention, which means that the vehicle mixes well with the molecule and does not lead to a significant decrease in the efficacy of the composition.

Examples of pharmaceutically acceptable vehicles or components thereof include: saccharides, such as sugars, for example, lactose, glucose and sucrose; starch, such as corn starch and potato starch; cellulose and derivatives thereof, such as sodium carboxymethyl cellulose, ethyl cellulose and methyl cellulose; tragacanth powder; malt; gelatin; talcum; solid lubricants, such as stearic acid and magnesium stearate; calcium sulfate; vegetable oils, such peanut oil, cottonseed oil, sesame oil, olive oil, corn oil and cocoa butter; polyols, such as propylene glycol, glycerin, sorbitol, mannitol and polyethylene glycol; alginic acid; emulsifier, such as Tween®; wetting agent, such as sodium lauryl sulfate; colorant; flavoring agent; tableting aid, stabilizer; antioxidant; preservative; pyrogen-free water; isotonic saline solution; and phosphate buffer; etc.

The pharmaceutical composition may be provided in different dosage forms to be administered at an amount beneficial to the patient, which may be determined by a physician according to known factors including species, age, bodyweight and general medical condition of the patient. Manners of administration include, for example, injection or other therapeutic processes.

The binding molecule of the invention may be used in a non-isolated or an isolated form. And, the binding molecule of the invention may be used alone or as a component of a mixture comprising at least one of the binding molecules of the invention (or a derivative or a fragment thereof). In other words, multiple binding molecules may be used in combination, such as in the case of a pharmaceutical composition comprising two or more of the binding molecules or variants or fragments thereof. For instance, binding molecules having activities complementary to each other or one another may be combined in a regimen for certain effect(s) of prevention, treatment or diagnosis; or, binding molecules having activity or activities in common may be combined in a regimen for certain effect(s) of prevention, treatment or diagnosis.

The binding molecule or the composition of the invention may be first tested in animal models before being applied to human beings. Animal models include, but are not limited to mice and monkeys.

The binding molecule of the invention may be administered at a suitable dosage of, for example, 0.001-100 mg/kg, preferably 0.01-15 mg/kg. For example, the administration may be a single bolus injection or scheduled multiple dosing. And, the dosages can be reduced or increased in proportion according to severity or emergency of the condition being treated. The molecule and the composition of the invention are preferably sterile. Methods of sterilization are well known to a person of ordinary skills in the art. Additional molecule(s) useful in relevant diagnosis, prevention and/or treatment may be administered in the same or similar way as the binding molecule of the invention. If desired, the additional molecule(s) may be administered separately before, simultaneously with or after the administration of one or more binding molecules or a pharmaceutical composition of the invention. Precise regimens for human patients are usually selected through clinical trials.

The binding molecule of the invention may be included in a suitable package, such as a kit, for convenience in clinical use. Preferably, the kit further comprises an instruction on administration.

Also included herein is a method of lowering serum cholesterol level or for treating or preventing diseases associated with high serum cholesterol level in patients. The method may include administering to the patient an effective amount of at least one of the monoclonal antibodies according to the invention. Preferably, the monoclonal antibody of the invention may be used in combination with an agent capable of increasing the availability of LDLR proteins. Examples of such agents include atorvastatin, cerivastatin, fluvastatin, lovastatin, mevastatin, pitavastatin, rosuvastatin, simvastatin, and combination of two or more of the above.

Immunoconjugates

In another aspect, the disclosure includes an immunoconjugate comprising at least one binding protein of the invention and at least one functional molecule (e.g., a detectable moiety/substance). The antibody and the functional molecule may be conjugated in various ways including covalent linkage, coupling, attachment, crosslinking, etc. The immunoconjugate of the invention may contain one or more label(s). The label(s) may also be covalently bound to/conjugated with the binding protein of the invention directly. Alternatively, the label(s) may be bound to/conjugated with the binding protein of the invention through one or more linker compound(s). Methods for conjugating the label(s) with the binding protein are well known to a person of ordinary skills in the art. The label of the immunoconjugate may also be a therapeutic agent.

The immunoconjugate may comprise an antibody according to the invention and a detectable label. Useful detectable labels include, but are not limited to fluorescent labels and chromogenic labels. Examples include enzymes, prosthetic groups/cofactors, fluorescent materials, luminescent materials, bioluminescent materials, radioactive materials, positron emission metals and non-radioactive paramagnetic metal ions. More than one label can be included. Selection of a label for certain detection and/or analysis and/or diagnosis depends on the specific technique(s) or methods used in said detection/analysis/diagnosis, such as immunohistochemical staining (tissue sample), flow cytometry etc. Labels suitable for using in various known technique(s) and methods of detection/analysis/diagnosis are known to a person of ordinary skills in the art.

Further, the human binding protein or the immunoconjugate of the invention may be immobilized on a solid support, particularly for immunoassay or purification of the PCSK9 protein or a fragment thereof in vitro. The solid support may be porous or non-porous, planar or non-planar. The binding protein of the invention may be fused with a tag sequence for ease of purification. Examples of the tag sequence include, but are not limited to hexa-histidine tag, hemagglutinin (HA) tag, myc tag or flag tag. Alternatively, an antibody may conjugate with a different antibody to form a heteroconjugate.

The binding protein (antibody) of the invention may comprise a leader peptide in sequence, or not. When being expressed by cells, a mature binding protein (antibody) does not include a leader peptide.

Detection Agents and Kits

The binding molecule of the invention makes it possible to provide agents and kits for a convenient, quick and accurate detection of PCSK9 level in a sample.

As used herein, the term "test sample" or "sample" includes various types of samples, including blood and other biological fluid, solid tissue samples, such as a biopsy tissue sample or a tissue culture, cells therein and off-springs thereof. This term also includes processed samples that have been subject to a process of, for example, reagent treatment, dissolution, enrichment for a certain component such as a protein or a nucleotide after harvesting.

Accordingly, a detection kit for detecting level of PCSK9 in a sample is provided. The kit comprises a PCSK9 binding molecule of the invention or an immunoconjugate of the PCSK9 binding molecule and a detectable label.

The PCSK9 binding molecule of the invention makes it possible to conveniently provide a detection kit for a specific detection of PCSK9 level.

To make the detection more convenient, the kit may further comprise one or more other detection agents or auxiliary agents in addition to the binding molecule or the immunoconjugate comprising the PCSK9 binding molecule and a detectable label according to the invention. Examples of auxiliary agent include those agents conventionally used in ELISA assays. Properties and preparation of these agents are well known to a person of ordinary skills in the art, and examples include developers, markers, labels, secondary antibodies, anti-antibodies, sensitizers, etc. It should be understood that the detection kit according to the invention can be in any forms, as long as it utilizes the binding molecule according to the invention as the recognizing agent for PCSK9.

Additionally, the kit may further comprise an instruction on how to use the agents contained therein.

The binding molecule and/or the kit according to the invention make it possible to detect the presence or content of PCSK9 in a sample of a subject using various immunological methods to indicate the presence or absence of a disease associated with abnormal expression or activity of PCSK9 in the subject.

The inventions will be described in further details by referring to the following specific examples. It should be understood that these examples are provided for illustration only and by no means to limit the scope of the invention. Experiments were conducted as specified or otherwise according to the conventional practices, such as the teachings in *Molecular Cloning: A Laboratory Manual* (J. Sambrook et al., 3$^{rd}$ Edition. 2002, Science Press, China), or according to manufacturers' instructions.

Example 1: Anti-PCSK9 Monoclonal Antibody—Optimization and Screen

Through extensive investigation and screening in en effort to find an eligible anti-PCSK9 antibody, the inventors obtained from human phage antibody library two strains of monoclonal antibodies with prominent performances. Nucleic acid sequences and amino acid sequences of their variable regions are identified as in the following.

1. Monoclonal Antibody B9287

The nucleotide sequence of the heavy-chain variable region is as set forth in SEQ ID NO: 1 (with a leader peptide) or SEQ ID NO: 21 (without leader peptide).

The amino acid sequence of the heavy-chain variable region is as set forth in SEQ ID NO: 2 (with a leader peptide) or SEQ ID NO: 22 (without leader peptide).

The amino acid sequences of the heavy-chain CDRs are as follows:

```
HCDR1:
                                    (SEQ ID NO: 7)
AFTFDSFGMH,

HCDR2:
                                    (SEQ ID NO: 8)
LLWSDGSDEYYADSAKG,
and

HCDR3:
                                    (SEQ ID NO: 9)
AVGAIYQFYAMDV.
```

The nucleotide sequences of the heavy-chain CDRs are as follows:

```
HCDR1:
                                    (SEQ ID NO: 14)
GCCTTCACCTTCGACAGCTTCGGCATGCAC;

HCDR2:
                                    (SEQ ID NO: 15)
CTGCTTTGGAGCGACGGCTCCGACGAGTACTACGCCGACTCCGC

TAAGGGC;
and

HCDR3:
                                    (SEQ ID NO: 16)
GCGGTGGGCGCCATCTACCAGTTCTACGCCATGGACGTG.
```

The nucleotide sequence of the light-chain variable region is as set forth in SEQ ID NO: 3 or SEQ ID NO: 23 (without leader peptide).

The amino acid sequence of the light-chain variable region is as set forth in SEQ ID NO: 4 or SEQ ID NO: 24 (without leader peptide).

The amino acid sequences of the CDRs in the light-chain are as follows:

```
LCDR1:
                                    (SEQ ID NO: 10)
TGTSSNIGNQFVS;
```

```
LCDR2:
                                        (SEQ ID NO: 11)
EYNKRPS;
and

LCDR3:
                                        (SEQ ID NO: 12)
GSWDSSLSGYV.
```

The nucleotide sequences of the light-chain CDRs are as follows:

```
LCDR1:
                                        (SEQ ID NO: 17)
ACCGGCACCTCCTCCAACATCGGCAACCAATTCGTGTCC;

LCDR2:
                                        (SEQ ID NO: 18)
GAGTACAACAAGCGGCCCTCC;
and LCDR3:
                                        (SEQ ID NO: 19)
GGCTCCTGGGACTCTTCCCTGTCCGGCTATGTG.
```

2. Monoclonal Antibody B9288

The nucleotide sequence of the heavy-chain variable region of the antibody is as set forth in SEQ ID NO: 5 or SEQ ID NO: 25 (without leader peptide).

The amino acid sequence of the heavy-chain variable region of the antibody is as set forth in SEQ ID NO: 6 or SEQ ID NO: 26 (without leader peptide).

The amino acid sequences of the heavy-chain CDRs are as follows:

```
HCDR1:
                                        (SEQ ID NO: 7)
AFTFDSFGMH;

HCDR2:
                                        (SEQ ID NO: 8)
LLWSDGSDEYYADSAKG;
and HCDR3:
                                        (SEQ ID NO: 13)
AVGSIYYYYAMDV.
```

The nucleotide sequences of the heavy-chain CDRs are as follows:

```
HCDR1:
                                        (SEQ ID NO: 14)
GCCTTCACCTTCGACAGCTTCGGCATGCAC;

HCDR2:
                                        (SEQ ID NO: 15)
CTGCTTTGGAGCGACGGCTCCGACGAGTACTACGCCGACTC
CGCTAAGGGC;
and HCDR3:
                                        (SEQ ID NO: 20)
GCGGTGGGCTCCATCTACTACTACTACGCCATGGACGTG.
```

Monoclonal antibody B9288 has the same light-chain and the same light-chain CDRs as B9287 in both amino acid sequences and nucleotide sequences.

Example 2: Production of Anti-PCSK9 Monoclonal Antibody by Transfected Cells

The nucleotide sequence of mAb B9287's heavy chain (SEQ ID NO: 1, with the encoding sequence of the leader peptide) was added with HindIII/NotI restrictive enzyme digestion sites at respective ends and inserted into the corresponding site on pCDNA3.1+ plasmid; and the nucleotide sequence of mAb B9287's light-chain (SEQ ID NO: 3, with the encoding sequence of the leader peptide) was added with HindIII/NotI restrictive enzyme digestion sites at respective ends and inserted into the corresponding site on pCDNA3.1+ plasmid; and the recombinant plasmids for expressing mAb B9287 were obtained thereby.

The nucleotide sequence of mAb B9288's heavy-chain (SEQ ID NO: 5, with the encoding sequence of the leader peptide) was added with HindIII/NotI restrictive enzyme digestion sites at respective ends and inserted into the corresponding site on pCDNA3.1+ plasmid, and the nucleotide sequence of mAb B9288's light-chain (SEQ ID NO: 3) was added with HindIII/NotI restrictive enzyme digestion sites at respective ends and inserted into the corresponding site on pCDNA3.1+ plasmid; and the recombinant plasmids for expressing mAb B9288 were obtained thereby.

1. Transient Transfection

The obtained recombinant expression plasmids for mAb B9287 or the recombinant expression plasmids for mAb B9288 were transfected into HEK293 cells in suspension by transient lipofection.

The transfected cells were cultured in Expi293 Expression Medium at 37° C., $CO_2$ 8%, 120 rpm.

Expansion cultures of the transfected cells were subject to a two-stage centrifugation (the first stage: 10 min at 1,000 g, and the second stage: 30 min at 10,000 g), and the supernatant was separated from cells and debris and harvested. The supernatant was loaded onto the affinity column of Protein A. A three-step rinsing (the rinsing buffers as in the order of steps: PB 150 mM NaCl pH 6.5; 20 mM Na-citrate 1 M NaCl pH 5.5; and 20 mM Na-citrate pH 5.5) was conducted to remove impurities. The target protein was isolated and captured by a linear pH gradient elution (starting buffer A: 20 mM Na-citrate pH 5.5; final buffer B: 20 mM Na-citrate pH 3.0). Finally, the target antibody was exchanged into the buffer of 200 mM HEPE, 100 mM NaCl, 50 mM NaOAc pH 7.0 by ultrafiltration concentration.

2. Electrotransfection to prepare Cells for Stable Expression of B9287

The obtained plasmids (20 µg of plasmid DNA in total) comprising the light-chain (SEQ ID NO: 23) and the heavy-chain (SEQ ID NO: 21) of B9287 were mixed with $1.0 \times 10^7$ CHO-K1 host cells. The mixture of the cells and the plasmids were loaded into a electroporator (Gene Pulser II) and subject to an electroporation using an exponential decay wave of 300V and 950 µf. The mixture of the electroporated cells and the remaining plasmid DNA molecules were added into 2 mL of host cell minimum medium (EX-CELL® Advanced™ CHO Fed-batch Medium, Sigma, supplemented with 6 mM L-glutamine, Sigma) in a 6-well plate. Cells were incubated in a $CO_2$ incubator at 37° C. for 24 h. The medium was then replaced with the selective growth medium (EX-CELL® Advanced™ CHO Fed-batch Medium, Sigma; supplemented with Puromycin, 20 µg/mL, GIBCO and 6 mM L-glutamine, Sigma) for a stress screen of around 3 weeks till a recovery of more than 90% cell viability to obtain the Pool line comprising the heavy-chain and the light-chain genes integrated into genome of the CHO-K1 cells. Upon the Pool cells recovered to more than 90% viability, the cells were Fed-batch cultured in a volume of 30 mL in a 125 mL-shake flask, starting from the initial concentration of $0.3 \times 10^6$ cells/mL. At day 3, 5, 7, 9, 11 and 13, supplement feed (Ex-CELL Advanced CHO feed 1 (with glucose). Sigma) was added, and samples were collected for measurement of cell density and viability. When glucose level dropped to 3 g/L, glucose was added to bring it back to 6 g/L. When cell viability fell below 70%, the culture was terminated and antibody concentration was determined.

3. Semi-Solid Cloning and ELISA Screening for Transfectants Stably Expressing B9287

Pool cells with high antibody expression levels were selected for monoclonal screen. Suspension containing 50-200 Pool cells were evenly mixed with 10 mL semi-solid medium (CloneMedia CHO Growth A with L-Gln, Molecular devices), and plated on a 100 mm petri dish. The cells were incubated in incubator at 37° C., 5% $CO_2$ for 14 days. Clones of medium size were selected and transferred onto a 96-well plate containing 200 μL selection medium per well for an incubation of 4-5 days. The cell suspension was mixed to homogenous by pipetting, then evenly divided into two aliquotes on two 96-well plates, and fresh medium was added to a culture volume of 200 μL. One of the plates was subject to routine amplification with medium replacement. Briefly, every time, 100 μL cell culture medium was drained and 100 μL fresh medium was supplemented. The other plate was subject to a 10-day continuous culture without medium replacement. The supernate was evaluated by ELISA. Cells for amplification and sub-cloning were selected according to OD measurements. The cell lines elected in the first round of semi-solid screening were plated at a density of 0.5 cells/well on a 96-well plate. Examination on cells started 7 days later, and continued till the clones grew to a certain magnitude for screening. Wells only containing a single clone were selected as single-cell wells. The cultures in the single-cell wells on the 96-well plate, which may be optionally diluted as appropriate, were transferred to a coated ELISA plate for screening by ELISA. The TOP 3 single-cell lines were selected and Fed-Batch cultured to confirm the expression level.

Example 3: The Characterizations of the Anti-PCSK9 Monoclonal Antibodies Via Biological Assays 1. Capillary Electrophoresis (CE-SDS)

The purities of the antibodies were evaluated via capillary electrophoresis on the LabChip GXII system. The results of the percentages of main peak purity and respective molecular weight for the anti-PCSK9 monoclonal antibodies of the invention (without leader peptide) under reducing and non-reducing conditions are summarized in Table 1 (non-reducing) and Table 2 (reducing).

TABLE 1

| ID# | Main Peak Purity % (non-reducing) | Molecular Weight (kDa) |
|---|---|---|
| B9287 | 77.4% | 177.67 |
| B9288 | 80.4% | 178.05 |

TABLE 2

| ID# | Main Peak Purity % (non-reducing) | Molecular Weight (kDa) |
|---|---|---|
| B9287 | 35.4%, 63.5% | 36.82, 65.35 |
| B9288 | 36.7%, 63.3% | 36.80, 65.72 |

2. Size-Exclusion Liquid Chromatography (SE-HPLC)

The monoclonal antibodies were filtered through a 0.2 μm filter (Thomson, Cat. No. 25535-100) and then loaded onto a MAbPac SEC-1 column (Thermo, Cat. No. 07469620). A buffer of 50 mM sodium phosphate, 300 mM NaCl, pH 6.2 was used as the mobile phase at 0.2 ml/min. Peak calculations were integrated using the ChemStation software. The purities of the main peak and high molecular weight (HMW) aggregates for the anti-PCSK9 monoclonal antibodies of the invention are summarized in Table 3.

TABLE 3

| ID# | Main Peak Purity % | HMW Aggregate Peak Purity % |
|---|---|---|
| B9287 | >99.9% | <0.01% |
| B9288 | >99.9% | <0.01% |

3. Protein Stability Evaluated by Differential Scanning Calorimetry

Differential scanning calorimetry (DSC) is a detection of differentia in heats required for a temperature rise between the sample and the reference as a function of temperature. It can be used to describe multiple properties of a protein, including the melting temperature ($T_M$) (i.e., the temperature at which 50% proteins are denatured), which is a measurement of protein stability.

The test antibody (1 mg/ml) was placed in the Nano DSC sample chamber. Temperature was raised from 25° C. to 100° C. at the rate of 1° C./min. Before the test, a 15-min pre-scan was performed to guarantee an accurate starting temperature. In the data of samples, the value of buffer alone was subtracted. Tm was calculated using Nano DSC software.

Results are summarized in Table 4.

TABLE 4

| ID# | Tm (° C.) |
|---|---|
| B9287 | 63° C., 74° C. |
| B9288 | 61° C., 73° C. |

Example 4: Characterization of the Binding Affinity of the Antibodies to PCSK9 Protein The binding ability of the anti-PCSK9 monoclonal antibodies to human, mouse or *Macaca fascicularis* PCSK9 was evaluated using the Octet Red96 system (ForteBio). Anti-human IgG Fc (AHC) kinetic-grade biosensor (Fortebio, #18-5063) was pre-treated by glycine at pH 1.7 and then soaked in the detection buffer. The PCSK9 monoclonal antibody (10 μg/ml) as the test sample was fixed on the AHC biosensor for 120 seconds. The biosensor loaded with the PCSK9 monoclonal antibody was then soaked in human PCSK9 antigen (GeneBank AX127530.1), mouse PCSK9 antigen (NCBI NM_153565.2) or *Macaca fascicularis* PCSK9 antigen (NCBI NM_001112660.1) at varying concentrations and buffer. For the test column, the end-point of dilution comprised the detection buffer only to detect the non-specific binding between the detection buffer and the loaded biosensor. Antigen-antibody binding was detected from the 80$^{th}$ to the 120$^{th}$ second, followed by dissociation from the 120$^{th}$ to the 180$^{th}$ second. The 60-second baseline was determined using the detection buffer. For the anti-PCSK9 monoclonal antibodies, the affinity curves were fitted using a kinetic sensor 1:1 monovalent binding model.

The kinetic analysis result is shown in FIG. 1 and Table 5.

TABLE 5

| Loading ID | Sample ID | KD (M) | kon(1/Ms) | kdis(1/s) | Full X^2 | Full R^2 |
|---|---|---|---|---|---|---|
| B9287 | huPCSK9 | <1.0E−12 | 3.09E+05 | <1.0E−07 | 0.0444 | 0.9989 |
| B9288 | huPCSK9 | <1.0E−12 | 2.52E+05 | <1.0E−07 | 0.016 | 0.9995 |
| B9287 | cynoPCSK9 | 2.9E−11 | 2.48E+05 | 7.21E−06 | 0.0102 | 0.9995 |
| B9288 | cynoPCSK9 | 4.1E−10 | 2.51E+05 | 1.03E−04 | 0.0126 | 0.999 |
| B9287 | msPCSK9 | 9.80E−09 | 2.70E+05 | 2.70E−03 | 0.0308 | 0.9994 |
| B9288 | msPCSK9 | 6.60E−09 | 1.40E+05 | 9.20E−04 | 0.0123 | 0.9994 |

Example 5: Cell LDL Uptake Analysis

Human HepG2 cells were plated in the DMEM medium (Mediatech, Inc) supplemented with 10% FBS at $5 \times 10^4$ cells/well in a dark transparent 96-well plate (Costar) and incubated at 37° C. (5% $CO_2$) overnight. Human PCSK9 (20 μg/ml) was incubated with antibody dilutions in the uptake buffer (DMEM supplemented with 10% FBS) at different concentrations or the buffer alone (control) at room temperature for 1 hour to form the PCSK9-antibody complexes. Supernate of the culture was decanted, and the PCSK9/antibody mixture was added, followed by Dil-LDL (Invitrogen) dilution at the final concentration of 8 μg/ml in the uptake buffer. After incubation at 37° C. (5% $CO_2$) for 16-18 hours, the cells were washed with PBS and fluorescent signal was measured using TECAN M1000 at 554 nm (excitation) and 571 nm (emission).

Figure 2:
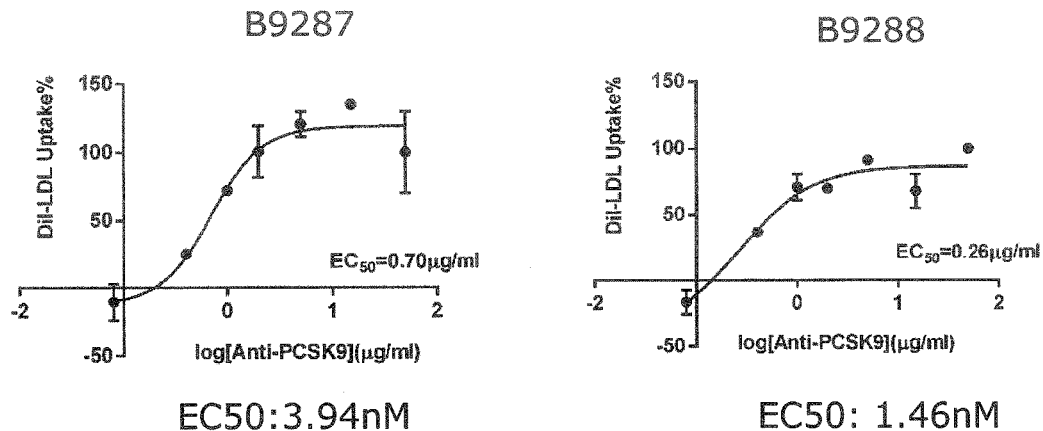
FIG. 2: Functional analysis of the antigen binding proteins of the invention in reducing LDL uptake in cells.

The results of cell LDL uptake are as shown in FIG. 2. Briefly, IC50 values of the anti-PCSK9 monoclonal antibodies were determined to be 3.94 nM (B9287) and 1.46 nM (B9288) pM (FIG. 2).

The results indicate that the antigen binding proteins according to the invention have excellent capacity of lowering LDL uptake by cells.

Example 6: Effect of Anti-PCSK9 Monoclonal Antibodies on Blood LDL in *Macaca rhesus* In Vivo In hyperlipemic *Macaca rhesus* monkeys, anti-PCSK9 mAb B9287 was evaluated for its effect in lowering serum LDL in a non-human primate animal disease model in vivo. Four *Macaca rhesus* monkeys (>7 years of age) having hyperlipemia were subcutaneously single injected with the vehicle (PBS+0.01% Tween20) or anti-PCSK9 mAb B9287 at the dosage of 3 mg/kg at day 0. Serum LDL was detected at day 0, 1, 3, 5, 7, 9, 11 and 14 after fasting overnight.

Figure 3:
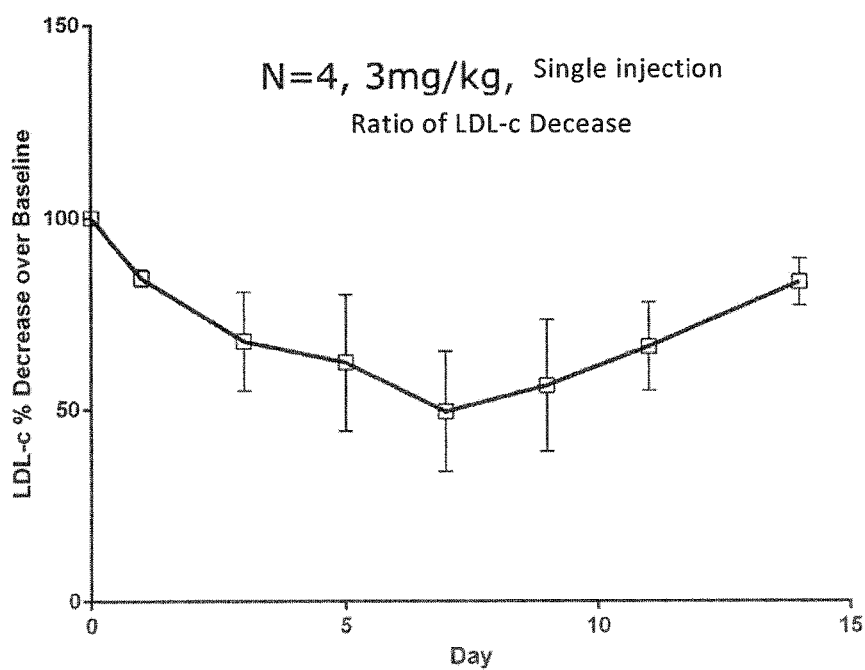
FIG. 3: effect of a preferred anti-PCSK9 antibody on serum LDL in hyperlipemic *Macaca rhesus* monkeys. Each group includes four male and female monkeys of >7 years of age. At day 0, the animals were subcutaneously administered with the specified amount of the preferred anti-PCSK9 antibody or an equal volume of saline. At the specified time points, plasma LDL was measured in plasma samples, in comparison with the plasma LDL measurement at day 0.

Results are as shown in FIG. 3. A single injection of 3 mg/kg of anti-PCSK9 mAb B9287 led to a significant drop in serum LDL (50% or more) in all the four animals.

The same test was conducted and the same result and capability of lowering serum LDL in *Macaca rhesus* in vivo was observed with anti-PCSK9 mAb B9288.

It is concluded that anti-PCSK9 antibodies decrease serum LDL level in non-human primate animal disease model.

All the references cited herein are incorporated by reference as each are individually cited by reference in their entirety. In view the foregoing, it will be obvious that certain changes and modifications as equivalents can be practiced within the scope of the appended claims.

What is claimed:

1. A PCSK9-specific binding protein comprising a light-chain variable region and a heavy-chain variable region, wherein,
the CDR1 of the heavy-chain variable region has the amino acid sequence as set forth in SEQ ID NO: 7;
the CDR2 of the heavy-chain variable region has the amino acid sequence as set forth in SEQ ID NO: 8;
the CDR3 of the heavy-chain variable region has the amino acid sequence as set forth in SEQ ID NO: 9 or the amino acid sequence as set forth in SEQ ID NO: 13;
the CDR1 of the light-chain variable region has the amino acid sequence as set forth in SEQ ID NO: 10;
the CDR2 of the light-chain variable region has the amino acid sequence as set forth in SEQ ID NO: 11; and
the CDR3 of the light-chain variable region has the amino acid sequence as set forth in SEQ ID NO: 12.

2. The PCSK9-specific binding protein according to claim 1, being selected from the group consisting of those wherein:
(a) the CDR1, CDR2 and CDR3 of the heavy-chain variable region have the amino acid sequences as set forth in SEQ ID NO: 7, SEQ ID NO: 8 and SEQ ID NO: 9, respectively; and the CDR1, CDR2 and CDR3 of the light-chain variable region have the amino acid sequences as set forth in SEQ ID NO: 10, SEQ ID NO: 11 and SEQ ID NO: 12, respectively; or
(b) the CDR1, CDR2 and CDR3 of the heavy-chain variable region have the amino acid sequences as set forth in SEQ ID NO: 7, SEQ ID NO: 8, SEQ ID NO: 13, respectively; and the CDR1, CDR2 and CDR3 of the light-chain variable region have the amino acid sequences as set forth in SEQ ID NO: 10, SEQ ID NO: 11 and SEQ ID NO: 12, respectively.

3. The PCSK9-specific binding protein according to claim 1, wherein
the heavy-chain variable region and the light-chain variable region have the amino acid sequences as set forth in SEQ ID NO: 2 and SEQ ID NO: 4, respectively; or
the heavy-chain variable region and the light-chain variable region have the amino acid sequences as set forth in SEQ ID NO: 6 and SEQ ID NO: 4, respectively; or
the heavy-chain variable region and the light-chain variable region have the amino acid sequences as set forth in SEQ ID NO: 22 and SEQ ID NO: 24, respectively; or
the heavy-chain variable region and the light-chain variable region have the amino acid sequences as set forth in SEQ ID NO: 26 and SEQ ID NO: 24, respectively.

4. A nucleic acid encoding the PCSK9-specific binding protein according to claim 1.

5. An expression vector, comprising the nucleic acid according to claim 4.

6. A host cell, comprising the expression vector according to claim 5.

7. A method for treating and/or preventing a disease associated with abnormal expression or activity of PCSK9; wherein said method comprising administrating the PCSK9-specific binding protein according to claim 1 to required patients.

8. The method of claim 7, wherein said disease associated with abnormal expression or activity of PCSK9 includes conditions associated with high serum cholesterol level.

9. The method of claim 8, wherein the disease is selected from the group consisting of hypercholesterolemia, coronary heart disease, metabolic syndrome and acute coronary syndrome.

10. A pharmaceutical composition, comprising:
an effective amount of the PCSK9-specific binding protein according to claim 1; and
a pharmaceutically acceptable vehicle.

11. A kit for treating and/or preventing a disease associated with abnormal expression or activity of PCSK9, wherein said kit comprises:
the PCSK9-specific binding protein according to claim 1; or
the pharmaceutical composition according to claim 10.

12. An immunoconjugate, comprising:
the PCSK9-specific binding protein according to claim 1; and
a detectable label.

13. The immunoconjugate of claim 12, wherein said detectable label is selected from the group consisting of fluorescent labels and chromogenic labels.

14. A detection kit for detecting the level of PCSK9, comprising:
   the PCSK9-specific binding protein according to claim 1; or
   the immunoconjugate according to claim 12.

15. A host cell, comprising the nucleic acid according to claim 4.

* * * * *

SEQUENCE LISTING

```
<160> NUMBER OF SEQ ID NOS: 26

<210> SEQ ID NO 1
<211> LENGTH: 1419
<212> TYPE: DNA
<213> ORGANISM: Homo Sapiens

<400> SEQUENCE: 1
atggacccca agggcagcct gagctggaga atcctgctgt tcctgagcct ggccttcgag      60
ctgagctacg gccaggtgca gctggtgcag tctggtgccg aagtgaagaa acccggctcc     120
tccgtgaagg tgtcctgcaa ggcctccgcc ttcaccttcg acagcttcgg catgcactgg     180
gtgcgacagg cccctggaca gggcctggaa tggatgggcc tgctttggag cgacggctcc     240
gacgagtact acgccgactc cgctaagggc cggttcacca tctcccggga caactccaag     300
```

```
aacaccctgt acctgcagat gaactccctg cggagcgacg acaccgccgt gtactactgt    360
gccagagcgg tgggcgccat ctaccagttc tacgccatgg acgtgtgggg ccagggcacc    420
acagtgaccg tgtcatctgc tagcaccaag ggcccatcgg tcttccccct ggcgccctgc    480
tccaggagca cctccgagag cacagcggcc ctgggctgcc tggtcaagga ctacttcccc    540
gaaccggtga cggtgtcgtg gaactcaggc gctctgacca gcggcgtgca caccttcccg    600
gctgtcctac agtcctcagg actctactcc ctcagcagcg tggtgaccgt gccctccagc    660
aacttcggca cccagaccta cacctgcaac gtagatcaca agcccagcaa caccaaggtg    720
gacaagacag ttgagcgcaa atgttgtgtc gagtgcccac cgtgcccagc accacctgtg    780
gcaggaccgt cagtcttcct cttcccccca aacccaagg acaccctcat gatctcccgg    840
acccctgagg tcacgtgcgt ggtggtggac gtgagccacg aagacccga ggtccagttc    900 aactggtacg tggacggcgt ggaggtgcat aatgccaaga caaagccacg ggaggagcag    960
ttcaacagca cgttccgtgt ggtcagcgtc ctcaccgttg tgcaccagga ctggctgaac   1020
ggcaaggagt acaagtgcaa ggtctccaac aaagcctcc cagcccccat cgagaaaacc   1080
atctccaaaa ccaaagggca gccccgagaa ccacaggtgt acaccctgcc cccatcccgg   1140
gaggagatga ccaagaacca ggtcagcctg acctgcctgg tcaaaggctt ctaccccagc   1200
gacatcgccg tggagtggga gagcaatggg cagccggaga acaactacaa gaccacacct   1260
cccatgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggttagtaa                          1419
```

<210> SEQ ID NO 2
<211> LENGTH: 471
<212> TYPE: PRT
<213> ORGANISM: Homo Sapiens

<400> SEQUENCE: 2

```
Met Asp Pro Lys Gly Ser Leu Ser Trp Arg Ile Leu Leu Phe Leu Ser
 1               5                  10                  15

Leu Ala Phe Glu Leu Ser Tyr Gly Gln Val Gln Leu Val Gln Ser Gly
             20                  25                  30

Ala Glu Val Lys Lys Pro Gly Ser Ser Val Lys Val Ser Cys Lys Ala
         35                  40                  45

Ser Ala Phe Thr Phe Asp Ser Phe Gly Met His Trp Val Arg Gln Ala
     50                  55                  60

Pro Gly Gln Gly Leu Glu Trp Met Gly Leu Leu Trp Ser Asp Gly Ser
 65                  70                  75                  80

Asp Glu Tyr Tyr Ala Asp Ser Ala Lys Gly Arg Phe Thr Ile Ser Arg
                 85                  90                  95

Asp Asn Ser Lys Asn Thr Leu Tyr Leu Gln Met Asn Ser Leu Arg Ser
            100                 105                 110

Asp Asp Thr Ala Val Tyr Tyr Cys Ala Arg Ala Val Gly Ala Ile Tyr
        115                 120                 125

Gln Phe Tyr Ala Met Asp Val Trp Gly Gln Gly Thr Thr Val Thr Val
    130                 135                 140

Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
                165                 170                 175
```

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Asn Phe Gly Thr
    210                 215                 220

Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Gln Phe Asn Trp Tyr Val
    290                 295                 300

Asp Gly Val Glu Val His Asn Ala Lys Thr Lys Pro Arg Glu Glu Gln
305                 310                 315                 320

Phe Asn Ser Thr Phe Arg Val Val Ser Val Leu Thr Val Val His Gln
                325                 330                 335

Asp Trp Leu Asn Gly Lys Glu Tyr Lys Cys Lys Val Ser Asn Lys Gly
            340                 345                 350

Leu Pro Ala Pro Ile Glu Lys Thr Ile Ser Lys Thr Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Met Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly
465                 470

<210> SEQ ID NO 3
<211> LENGTH: 714
<212> TYPE: DNA
<213> ORGANISM: Homo Sapiens

<400> SEQUENCE: 3
atgtccgtgc ctacccaggt gctgggactg ctgctgctgt ggctgaccga cgccagatgt    60
cagtctgctc tgacccagcc tccttccgtg tctggctctc ctggccagtc cgtgaccatc   120
tcctgcaccg gcacctcctc caacatcggc aaccaattcg tgtcctggta tcagcagctg   180
cccggcaccg ctcccaaact gatgatctac gagtacaaca gcggccctc  ggcgtgccc    240 gaccggttct ctggatctaa gtccggcaac accgcctccc tgaccatcag cggactgcag   300
acaggcgacg aggccgacta ctactgcggc tcctgggact cttccctgtc cggctatgtg   360
ttcggcaccg gcaccagagt gaccgtgctg ggacagccta aggccgctcc ttccgtgacc   420

| | |
|---|---|
| ctgttccctc atcctccga ggaactgcag gccaacaagg ccaccctcgt gtgcctgatc | 480 |
| tccgacttct accctggcgc cgtgaccgtg gcctggaagg ctgatagctc tcctgtgaag | 540 |
| gccggcgtgg aaaccaccac cccttccaag cagtccaaca caaatacgc cgcctcctcc | 600 |
| tacctgtccc tgaccctga gcagtggaag tcccaccggt cctacagctg ccaagtgacc | 660 |
| cacgagggct ccaccgtgga aaagaccgtg gctcctaccg agtgctcctg ataa | 714 |

<210> SEQ ID NO 4
<211> LENGTH: 236
<212> TYPE: PRT
<213> ORGANISM: Homo Sapiens

<400> SEQUENCE: 4

Met Ser Val Pro Thr Gln Val Leu Gly Leu Leu Leu Trp Leu Thr
1               5                   10                  15

Asp Ala Arg Cys Gln Ser Ala Leu Thr Gln Pro Ser Val Ser Gly
            20                  25                  30

Ser Pro Gly Gln Ser Val Thr Ile Ser Cys Thr Gly Thr Ser Ser Asn
        35                  40                  45

Ile Gly Asn Gln Phe Val Ser Trp Tyr Gln Gln Leu Pro Gly Thr Ala
50                  55                  60

Pro Lys Leu Met Ile Tyr Glu Tyr Asn Lys Arg Pro Ser Gly Val Pro
65                  70                  75                  80

Asp Arg Phe Ser Gly Ser Lys Ser Gly Asn Thr Ala Ser Leu Thr Ile
                85                  90                  95

Ser Gly Leu Gln Thr Gly Asp Glu Ala Asp Tyr Tyr Cys Gly Ser Trp
            100                 105                 110

Asp Ser Ser Leu Ser Gly Tyr Val Phe Gly Thr Gly Thr Arg Val Thr
        115                 120                 125

Val Leu Gly Gln Pro Lys Ala Ala Pro Ser Val Thr Leu Phe Pro Pro
130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235

<210> SEQ ID NO 5
<211> LENGTH: 1419
<212> TYPE: DNA
<213> ORGANISM: Homo Sapiens

<400> SEQUENCE: 5

| | |
|---|---|
| atggacccca agggcagcct gagctggaga atcctgctgt cctgagcct ggccttcgag | 60 |
| ctgagctacg gccaggtgca gctggtgcag tctggtgccg aagtgaagaa accggctcc | 120 |
| tccgtgaagg tgtcctgcaa ggcctccgcc ttcaccttcg acagcttcgg catgcactgg | 180 |
| gtgcgacagg ccccctggaca gggcctggaa tggatgggcc tgctttggag cgacggctcc | 240 |

```
gacgagtact acgccgactc cgctaagggc cggttcacca tctcccggga caactccaag    300
aacaccctgt acctgcagat gaactccctg cggagcgacg acaccgccgt gtactactgt    360
gccagagcgg tgggctccat ctactactac tacgccatgg acgtgtgggg ccagggcacc    420
acagtgaccg tgtcatctgc tagcaccaag ggcccatcgg tcttccccct ggcgccctgc    480
tccaggagca cctccgagag cacagcggcc ctgggctgcc tggtcaagga ctacttcccc    540
gaaccggtga cggtgtcgtg gaactcaggc gctctgacca gcggcgtgca caccttcccg    600
gctgtcctac agtcctcagg actctactcc ctcagcagcg tggtgaccgt gccctccagc    660
aacttcggca cccagaccta cacctgcaac gtagatcaca agcccagcaa caccaaggtg    720
gacaagacag ttgagcgcaa atgttgtgtc gagtgcccac cgtgcccagc accacctgtg    780
gcaggaccgt cagtcttcct cttccccccA aaacccaagg acaccctcat gatctcccgg    840 accccctgagg tcacgtgcgt ggtggtggac gtgagccacg aagaccccga ggtccagttc    900
aactggtacg tggacggcgt ggaggtgcat aatgccaaga caaagccacg ggaggagcag    960
ttcaacagca cgttccgtgt ggtcagcgtc ctcaccgttg tgcaccagga ctggctgaac   1020
ggcaaggagt acaagtgcaa ggtctccaac aaaggcctcc cagcccccat cgagaaaacc   1080
atctccaaaa ccaaagggca gccccgagaa ccacaggtgt acaccctgcc cccatcccgg   1140
gaggagatga ccaagaacca ggtcagcctg acctgcctgg tcaaaggctt ctaccccagc   1200
gacatcgccg tggagtggga gagcaatggg cagccggaga caactacaa gaccacacct   1260 cccatgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggttagtaa                            1419
```

<210> SEQ ID NO 6
<211> LENGTH: 471
<212> TYPE: PRT
<213> ORGANISM: Homo Sapiens

<400> SEQUENCE: 6

```
Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Ala Glu Val Lys Lys Pro Gly Ser Val Lys Val Ser Cys Lys Ala
        35                  40                  45

Ser Ala Phe Thr Phe Asp Ser Phe Gly Met His Trp Val Arg Gln Ala
    50                  55                  60

Pro Gly Gln Gly Leu Glu Trp Met Gly Leu Leu Trp Ser Asp Gly Ser
65                  70                  75                  80

Asp Glu Tyr Tyr Ala Asp Ser Ala Lys Gly Arg Phe Thr Ile Ser Arg
                85                  90                  95

Asp Asn Ser Lys Asn Thr Leu Tyr Leu Gln Met Asn Ser Leu Arg Ser
            100                 105                 110

Asp Asp Thr Ala Val Tyr Tyr Cys Ala Arg Ala Val Gly Ser Ile Tyr
        115                 120                 125

Tyr Tyr Tyr Ala Met Asp Val Trp Gly Gln Gly Thr Thr Val Thr Val
    130                 135                 140

Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
```

```
            165                 170                 175
Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Asn Phe Gly Thr
    210                 215                 220

Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Gln Phe Asn Trp Tyr Val
    290                 295                 300

Asp Gly Val Glu Val His Asn Ala Lys Thr Lys Pro Arg Glu Glu Gln
305                 310                 315                 320

Phe Asn Ser Thr Phe Arg Val Val Ser Val Leu Thr Val Val His Gln
                325                 330                 335

Asp Trp Leu Asn Gly Lys Glu Tyr Lys Cys Lys Val Ser Asn Lys Gly
            340                 345                 350

Leu Pro Ala Pro Ile Glu Lys Thr Ile Ser Lys Thr Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Met Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly
465                 470

<210> SEQ ID NO 7
<211> LENGTH: 10
<212> TYPE: PRT
<213> ORGANISM: Homo Sapiens

<400> SEQUENCE: 7

Ala Phe Thr Phe Asp Ser Phe Gly Met His
1               5                   10

<210> SEQ ID NO 8
<211> LENGTH: 17
<212> TYPE: PRT
<213> ORGANISM: Homo Sapiens

<400> SEQUENCE: 8

Leu Leu Trp Ser Asp Gly Ser Asp Glu Tyr Tyr Ala Asp Ser Ala Lys
```

Gly

<210> SEQ ID NO 9
<211> LENGTH: 13
<212> TYPE: PRT
<213> ORGANISM: Homo Sapiens

<400> SEQUENCE: 9

Ala Val Gly Ala Ile Tyr Gln Phe Tyr Ala Met Asp Val
1               5                   10

<210> SEQ ID NO 10
<211> LENGTH: 13
<212> TYPE: PRT
<213> ORGANISM: Homo Sapiens

<400> SEQUENCE: 10

Thr Gly Thr Ser Ser Asn Ile Gly Asn Gln Phe Val Ser
1               5                   10

<210> SEQ ID NO 11
<211> LENGTH: 7
<212> TYPE: PRT
<213> ORGANISM: Homo Sapiens

<400> SEQUENCE: 11

Glu Tyr Asn Lys Arg Pro Ser
1               5

<210> SEQ ID NO 12
<211> LENGTH: 11
<212> TYPE: PRT
<213> ORGANISM: Homo Sapiens

<400> SEQUENCE: 12

Gly Ser Trp Asp Ser Ser Leu Ser Gly Tyr Val
1               5                   10

<210> SEQ ID NO 13
<211> LENGTH: 13
<212> TYPE: PRT
<213> ORGANISM: Homo Sapiens

<400> SEQUENCE: 13

Ala Val Gly Ser Ile Tyr Tyr Tyr Tyr Ala Met Asp Val
1               5                   10

<210> SEQ ID NO 14
<211> LENGTH: 30
<212> TYPE: DNA
<213> ORGANISM: Homo Sapiens

<400> SEQUENCE: 14
gccttcacct tcgacagctt cggcatgcac                                    30

<210> SEQ ID NO 15
<211> LENGTH: 51
<212> TYPE: DNA
<213> ORGANISM: Homo Sapiens

<400> SEQUENCE: 15
ctgctttgga gcgacggctc cgacgagtac tacgccgact ccgctaaggg c            51

<210> SEQ ID NO 16
<211> LENGTH: 39
<212> TYPE: DNA
<213> ORGANISM: Homo Sapiens

<400> SEQUENCE: 16
gcggtgggcg ccatctacca gttctacgcc atggacgtg                              39

<210> SEQ ID NO 17
<211> LENGTH: 39
<212> TYPE: DNA
<213> ORGANISM: Homo Sapiens

<400> SEQUENCE: 17
accggcacct cctccaacat cggcaaccaa ttcgtgtcc                              39

<210> SEQ ID NO 18
<211> LENGTH: 21
<212> TYPE: DNA
<213> ORGANISM: Homo Sapiens

<400> SEQUENCE: 18
gagtacaaca agcggccctc c                                                 21

<210> SEQ ID NO 19
<211> LENGTH: 33
<212> TYPE: DNA
<213> ORGANISM: Homo Sapiens

<400> SEQUENCE: 19
ggctcctggg actcttccct gtccggctat gtg                                    33

<210> SEQ ID NO 20
<211> LENGTH: 39
<212> TYPE: DNA
<213> ORGANISM: Homo Sapiens

<400> SEQUENCE: 20
gcggtgggct ccatctacta ctactacgcc atggacgtg                              39

<210> SEQ ID NO 21
<211> LENGTH: 1347
<212> TYPE: DNA
<213> ORGANISM: Homo Sapiens

<400> SEQUENCE: 21
caggtgcagc tggtgcagtc tggtgccgaa gtgaagaaac cggctcctc cgtgaaggtg         60 tcctgcaagg cctccgcctt caccttcgac agcttcggca tgcactgggt gcgacaggcc       120
cctggacagg gcctggaatg gatgggcctg cttttggagcg acggctccga cgagtactac      180
gccgactccg ctaagggccg gttcaccatc tcccgggaca actccaagaa caccctgtac       240
ctgcagatga actccctgcg gagcgacgac accgccgtgt actactgtgc cagagcggtg       300
ggcgccatct accagttcta cgccatggac gtgtgggggcc agggcaccac agtgaccgtg      360
tcatctgcta gcaccaaggg cccatcggtc ttccccctgg cgccctgctc caggagcacc       420
tccgagagca gcggggccct gggctgcctg gtcaaggact acttccccga accggtgacg       480
gtgtcgtgga actcaggcgc tctgaccagc ggcgtgcaca ccttcccggc tgtcctacag       540
tcctcaggac tctactccct cagcagcgtg gtgaccgtgc cctccagcaa cttcggcacc       600
cagacctaca cctgcaacgt agatcacaag cccagcaaca ccaaggtgga caagacagtt       660

```
gagcgcaaat gttgtgtcga gtgcccaccg tgcccagcac cacctgtggc aggaccgtca    720
gtcttcctct ccccccaaa acccaaggac accctcatga tctcccggac ccctgaggtc     780
acgtgcgtgg tggtggacgt gagccacgaa gaccccgagg tccagttcaa ctggtacgtg    840
gacggcgtga aggtgcataa tgccaagaca aagccacggg aggagcagtt caacagcacg    900
ttccgtgtgg tcagcgtcct caccgttgtg caccaggact ggctgaacgg caaggagtac    960
aagtgcaagg tctccaacaa aggcctccca gcccccatcg agaaaaccat ctccaaaacc   1020
aaagggcagc cccgagaacc acaggtgtac accctgcccc catcccggga ggagatgacc   1080
aagaaccagg tcagcctgac ctgcctggtc aaaggcttct accccagcga catcgccgtg   1140
gagtgggaga gcaatgggca gccggagaac aactacaaga ccacacctcc catgctggac   1200
tccgacggct ccttcttcct ctacagcaag ctcaccgtgg acaagagcag gtggcagcag   1260
gggaacgtct tctcatgctc cgtgatgcat gaggctctgc acaaccacta cacgcagaag   1320
agcctctccc tgtctccggg ttagtaa                                       1347
```

<210> SEQ ID NO 22
<211> LENGTH: 447
<212> TYPE: PRT
<213> ORGANISM: Homo Sapiens

<400> SEQUENCE: 22

```
Gln Val Gln Leu Val Gln Ser Gly Ala Glu Val Lys Lys Pro Gly Ser
1               5                   10                  15

Ser Val Lys Val Ser Cys Lys Ala Ser Ala Phe Thr Phe Asp Ser Phe
                20                  25                  30

Gly Met His Trp Val Arg Gln Ala Pro Gly Gln Gly Leu Glu Trp Met
            35                  40                  45

Gly Leu Leu Trp Ser Asp Gly Ser Asp Glu Tyr Tyr Ala Asp Ser Ala
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Asp Asp Thr Ala Val Tyr Tyr Cys
                85                  90                  95

Ala Arg Ala Val Gly Ala Ile Tyr Gln Phe Tyr Ala Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
```

```
                    245                 250                 255
Thr Pro Glu Val Thr Cys Val Val Asp Val Ser His Glu Asp Pro
        260                 265                 270
Glu Val Gln Phe Asn Trp Tyr Val Asp Gly Val Glu Val His Asn Ala
    275                 280                 285
Lys Thr Lys Pro Arg Glu Glu Gln Phe Asn Ser Thr Phe Arg Val Val
    290                 295                 300
Ser Val Leu Thr Val Val His Gln Asp Trp Leu Asn Gly Lys Glu Tyr
305                 310                 315                 320
Lys Cys Lys Val Ser Asn Lys Gly Leu Pro Ala Pro Ile Glu Lys Thr
                325                 330                 335
Ile Ser Lys Thr Lys Gly Gln Pro Arg Glu Pro Gln Val Tyr Thr Leu
                340                 345                 350
Pro Pro Ser Arg Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Met Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly
            435                 440                 445

<210> SEQ ID NO 23
<211> LENGTH: 654
<212> TYPE: DNA
<213> ORGANISM: Homo Sapiens

<400> SEQUENCE: 23
cagtctgctc tgacccagcc tccttccgtg tctggctctc ctggccagtc cgtgaccatc      60
tcctgcaccg gcacctcctc caacatcggc aaccaattcg tgtcctggta tcagcagctg     120
cccggcaccg ctcccaaact gatgatctac gagtacaaca gcggccctc ggcgtgccc      180 gaccggttct ctggatctaa gtccggcaac accgcctccc tgaccatcag cggactgcag     240
acaggcgacg aggccgacta ctactgcggc tcctgggact cttccctgtc cggctatgtg     300
ttcggcaccg gcaccagagt gaccgtgctg gacagcctaa ggccgctcc ttccgtgacc     360 ctgttccctc catcctccga ggaactgcag gccaacaagg ccaccctcgt gtgcctgatc     420
tccgacttct accctggcgc cgtgaccgtg gcctggaagg ctgatagctc tcctgtgaag     480
gccggcgtgg aaaccaccac cccttccaag cagtccaaca caaatacgc cgcctcctcc     540 tacctgtccc tgacccctga gcagtggaag tcccaccggt cctacagctg ccaagtgacc     600
cacgagggct ccaccgtgga aaagaccgtg gctcctaccg agtgctcctg ataa           654

<210> SEQ ID NO 24
<211> LENGTH: 216
<212> TYPE: PRT
<213> ORGANISM: Homo Sapiens

<400> SEQUENCE: 24

Gln Ser Ala Leu Thr Gln Pro Pro Ser Val Ser Gly Ser Pro Gly Gln
1               5                   10                  15
```

Ser Val Thr Ile Ser Cys Thr Gly Thr Ser Ser Asn Ile Gly Asn Gln
            20                  25                  30

Phe Val Ser Trp Tyr Gln Gln Leu Pro Gly Thr Ala Pro Lys Leu Met
        35                  40                  45

Ile Tyr Glu Tyr Asn Lys Arg Pro Ser Gly Val Pro Asp Arg Phe Ser
 50                  55                  60

Gly Ser Lys Ser Gly Asn Thr Ala Ser Leu Thr Ile Ser Gly Leu Gln
 65                  70                  75                  80

Thr Gly Asp Glu Ala Asp Tyr Tyr Cys Gly Ser Trp Asp Ser Ser Leu
                85                  90                  95

Ser Gly Tyr Val Phe Gly Thr Gly Thr Arg Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
210                 215

<210> SEQ ID NO 25
<211> LENGTH: 1347
<212> TYPE: DNA
<213> ORGANISM: Homo Sapiens

<400> SEQUENCE: 25
caggtgcagc tggtgcagtc tggtgccgaa gtgaagaaac ccggctcctc cgtgaaggtg     60
tcctgcaagg cctccgcctt caccttcgac agcttcggca tgcactgggt gcgacaggcc    120
cctggacagg gcctggaatg gatgggcctg ctttggagcg acggctccga cgagtactac    180
gccgactccg ctaagggccg gttcaccatc tcccgggaca ctccaagaa caccctgtac    240 ctgcagatga actccctgcg gagcgacgac accgccgtgt actactgtgc cagagcggtg    300
ggctccatct actactacta cgccatggac gtgtggggcc agggcaccac agtgaccgtg    360
tcatctgcta gcaccaaggg cccatcggtc ttccccctgg cgccctgctc caggagcacc    420
tccgagagca cagcggccct gggctgcctg gtcaaggact acttccccga accggtgacg    480
gtgtcgtgga actcaggcgc tctgaccagc ggcgtgcaca ccttcccggc tgtcctacag    540
tcctcaggac tctactccct cagcagcgtg gtgaccgtgc cctccagcaa cttcggcacc    600
cagacctaca cctgcaacgt agatcacaag cccagcaaca ccaaggtgga caagacagtt    660
gagcgcaaat gttgtgtcga gtgcccaccg tgcccagcac cacctgtggc aggaccgtca    720
gtcttcctct tccccccaaa acccaaggac accctcatga tctcccggac ccctgaggtc    780
acgtgcgtgg tggtggacgt gagccacgaa gaccccgagg tccagttcaa ctggtacgtg    840
gacggcgtgg aggtgcataa tgccaagaca aagccacggg aggagcagtt caacagcacg    900
ttccgtgtgg tcagcgtcct caccgttgtg caccaggact ggctgaacgg caaggagtac    960

-continued

```
aagtgcaagg tctccaacaa aggcctccca gcccccatcg agaaaaccat ctccaaaacc      1020
aaagggcagc cccgagaacc acaggtgtac accctgcccc catcccggga ggagatgacc      1080
aagaaccagg tcagcctgac ctgcctggtc aaaggcttct accccagcga catcgccgtg      1140
gagtgggaga gcaatgggca gccggagaac aactacaaga ccacacctcc catgctggac      1200
tccgacggct ccttcttcct ctacagcaag ctcaccgtgg acaagagcag gtggcagcag      1260
gggaacgtct tctcatgctc cgtgatgcat gaggctctgc acaaccacta cacgcagaag      1320
agcctctccc tgtctccggg ttagtaa                                         1347

<210> SEQ ID NO 26
<211> LENGTH: 447
<212> TYPE: PRT
<213> ORGANISM: Homo Sapiens

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Ala Phe Thr Phe Asp Ser Phe
            20                  25                  30

Gly Met His Trp Val Arg Gln Ala Pro Gly Gln Gly Leu Glu Trp Met
        35                  40                  45

Gly Leu Leu Trp Ser Asp Gly Ser Asp Glu Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Asp Asp Thr Ala Val Tyr Tyr Cys
                85                  90                  95

Ala Arg Ala Val Gly Ser Ile Tyr Tyr Tyr Ala Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300
```

```
Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
            435                 440                 445
```